United States Patent
Rudi et al.

(12)

(10) Patent No.: US 6,617,138 B1
(45) Date of Patent: Sep. 9, 2003

(54) NUCLEIC ACID DETECTION METHOD (75) Inventors: Knut Rudi, Oslo (NO); Kjetill Sigurd Jakobsen, Olso (NO)

(73) Assignee: Genpoint AS, Oslo (NO)

( * ) Notice: Subject to any disclaimer, the term of this patent is extended or adjusted under 35 U.S.C. 154(b) by 0 days.

(21) Appl. No.: 09/646,847

(22) PCT Filed: Apr. 1, 1999

(86) PCT No.: PCT/GB99/01025

§ 371 (c)(1),
(2), (4) Date: Feb. 2, 2001

(87) PCT Pub. No.: WO99/50448

PCT Pub. Date: Oct. 7, 1999

(30) Foreign Application Priority Data

Apr. 1, 1998 (GB) ............................................. 9807045

(51) Int. Cl.[7] ................................................. C12P 19/34
(52) U.S. Cl. ........................... 435/91.2; 435/91.1; 435/6
(58) Field of Search ............................... 435/91.2, 91.1, 435/6

(56) References Cited

U.S. PATENT DOCUMENTS 5,710,028 A * 1/1998 Eyal et al. .................. 435/91.1

OTHER PUBLICATIONS

Luis Ugozzoli Johanna M. Wahlqvist, Ali Ehsani, Bruce E. Kaplan, and R. Bruce Wallace Detection of Specific Alleles by Using Allele–Specific Primer Extention Followed by Capture on Solid Support pp. 107–112 in GATA, vol. 19, No. 4, 1992.*

Knut Rudd, Olav M. Skulberg, Frank Larsen and Kjetill S Jakobsen Strain Characterization and Classification of Oxphotobacteria in Clone Cultures on the Basis of 16S rRna Sequences from the Variable Regions V6, V7, and V8 vol. 63, No. 7, pp. 2639–2643. 1998.*

Tomi Pastinen, Jukka Partanen and Ann–Christine Syvanen Multiplex, fluorescent, solid–phase minisequencing for efficient screening of DNA sequence variation Clinical Chemistry 42:9 pp. 1391–1397, 1996.*

Paul D. Siebert and James W. Larrick Competitive PCR pp. 557–558 Nature vol. 359 1992.*

* cited by examiner

Primary Examiner—Jeffrey Fredman
Assistant Examiner—Juliet Einsmann
(74) Attorney, Agent, or Firm—Dorsey & Whitney LLP (57) ABSTRACT A method of detecting a target nucleotide sequence in a nucleic acid molecule, which comprises: (a) binding of an oligonucleotide probe to said nucleic acid molecule; (b) selective labelling of the bound oligonucleotide probe in the presence of said target nucleotide sequence; (c) hybridization of the labelled oligonucleotide to a complementary sequence; and (d) subsequent detection of the label; such methods being suitable for qualitative and quantitative assays of microbiological populations.

20 Claims, 6 Drawing Sheets

NUCLEIC ACID DETECTION METHOD

The present invention relates to nucleic acid detection methods, in particular to quantitative nucleic acid detection methods.

Detection, especially quantitative detection of a particular nucleic acid sequence, as an indication of the presence of an organism e.g. a pathogen in a clinical sample or a contaminant in a food or environmental sample, such as toxin-producing cyanobacteria in water sources, or of mRNA to show a change in transcription levels, is a valuable microbiological tool. In addition, in the diagnostic or forensic use of nucleic acid analysis or in the study of polymorphisms, full sequencing of the target nucleic acid may be unnecessary where the detection of a single base variation or mismatch is sufficient to give a positive identification. Such a single base variation or mismatch may, for example, arise from allelic variation or polymorphism, a point mutation, or any deletion or insertion of genetic material where the detection of a single abnormal or species specific base will give the required information.

Through our work in the development of methods for the detection of bacteria in water, we have developed a new nucleic acid detection method suitable for a wide variety of applications in the environmental, agricultural, food, veterinary, health and medical fields and indeed as a general tool in molecular biology.

There are a number of techniques available for the analysis of nucleic acids including the manufacture of synthetic oligonucleotide probes, particularly labelled probes, for hybridisation to target sequences; in vitro amplification of target nucleic acid sequences by PCR and other related amplification methods and (automated) direct DNA sequencing. These have led to the development of novel approaches for the detection and characterisation of nucleic acids in environmental monitoring (Bej, A. K. and Mahbubani, M. H. [1994] in PCR Technology: Current Innovations p 327–339 and Bowman, J. P. and Sayler, G. S. [1996] in Molecular approaches to environmental microbiology p 63–97). There are three main strategies for quantification of amplified DNA; i.e. size separation by electrophoresis, hybridization to capture probes, and real-time detection. The problems with the gel electrophoresis method are the detection of multiple targets in a single reaction, and interpretation of the results. Size separation detection of multiplex amplifications is also difficult to achieve because the amplification ratios of amplicons with different sizes are dependent on DNA quality.

The capture probe assay is based on hybridization of the entire amplified fragments. Evidently, this assay is not suitable for separation and quantification of homologous amplicons, e.g. products of competitive amplifications. The different amplicons will form sandwich hybridizations at the homologous sites, leading to the capture of both target and non-target fragments, even if the capture site is discriminating.

The ABI PRISM™ 7700 Sequence Detection System (Perkin Elmer, Foster City, Calif.) provides real-time quantitative PCR amplification. However, multiplex assays are limited by the number of fluorochromes available and their overlapping fluorescent spectra.

It is always an aim in nucleic acid detection methods to increase their specificity, ie. to reduce non-specific binding or detection of a non-specific background signal. A separate but associated goal is to increase the sensitivity of the detection method, ie. to allow measurement of very small amounts of target nucleic acid.

It would also represent a significant advantage if the method allowed the detection and quantification of several, preferably a large number such as 10 or more, polymorphic sites in a single reaction e.g. allowing the detection and quantification of several different target organisms in a single multiplex assay.

We have developed a convenient detection method which provides good sensitivity and specificity and the ability to detect and quantitate a large number of polymorphic sites in a single reaction. In particular, the methods represent significant advantages over those employing agarose gel electrophoresis or direct detection of the amplified DNA in the quantification.

The invention thus provides a method of detecting a target nucleotide sequence in a nucleic acid molecule, which comprises:

(a) binding of an oligonucleotide probe to said nucleic acid molecule;

(b) selective labelling of the bound oligonucleotide probe in the presence of said target nucleotide sequence;

(c) hybridisation of the labelled oligonucleotide to a complementary sequence; and (d) subsequent detection of the label.

The method of the invention can be used in the detection of all target nucleotide sequences, such as DNA sequences, particularly DNA resulting from PCR amplification cycles. The DNA may be native or cDNA formed from mRNA by reverse transcriptase. The DNA may be single or double stranded, linear or circular. The target nucleic acid may be RNA, e.g. mRNA or in particular ribosomal RNA which is present in a cell in multiple copies, for example 3,000–20,000 copies per cell.

In the context of the present invention, the term "nucleotide sequence" may refer to a 'sequence' of only one nucleotide in length, where the nucleic acid of interest differs by only one nucleotide from other (non-target) sequences which it is not desired to detect, such as in the case of detection of a point mutation or polymorphism. More usually, the nucleotide sequence to be detected is characteristic of a particular nucleic acid or group of nucleic acids or of a particular organism or group of organisms e.g. a species, where it is desired to detect the presence of that target (e.g. the nucleic acid/or organism) in a sample containing a number of different molecules or organisms, such as in the detection of particular bacteria e.g. in a clinical or environmental sample.

The oligonucleotide probe may comprise 5 to 50, preferably 10 to 40, more preferably 20 to 30 nucleotides. The probe is selected to bind to the target nucleic acid, namely the nucleic acid molecule containing the target nucleotide sequence. The oligonucleotide is conveniently sufficiently large to provide appropriate hybridisation to the target nucleic acid, yet still reasonably short in order to avoid unnecessary chemical synthesis. Methods for oligonucleotide production are standard in the art.

As discussed above, the target nucleic acid may be DNA, cDNA or RNA. The oligonucleotide probe is designed to bind to a target region in the nucleic acid molecule containing the target nucleotide sequence. "Target region" is used herein to refer to the sequence of nucleic acid which binds to the oligonucleotide probe. This target region may be in the form of a "signature sequence" which characterises a particular nucleic acid or group of nucleic acids or organisms etc. or may be the section of nucleic acid immediately preceding a single base position of interest, if a polymorphism, point mutation, insertion or deletion is to be detected.

It is of course desirable that the target region be absent from any non-target molecules in the sample in order to introduce selectivity between target and non-target nucleotide sequences. This specificity of binding may be achieved by incorporating into the probe regions of complementarity or substantial complementarity to the desired target region and/or mismatches to non-target sequences. The region of complementarity may be present at terminal or internal segments of the probe, or both.

Conventionally, nucleic acid detection methods have involved labelling of the oligonucleotide probe prior to hybridisation to the target nucleic acid sequence. However, in our method, labelling of the probe is dependent upon the sequence of the nucleic acid molecule to which the probe is bound. In other words labelling of the probe is template-sequence dependent (i.e. sequence-specific)—incorporation of the label will is only occur in the presence of a desired or selected "sequence" in the target molecule, which may be in the target region or in the target nucleotide sequence itself, or it will occur selectively ie. the step of label incorporation into the oligonucleotide probe may be discriminating (ie. based on a "mini-sequencing" principle). This adds an extra dimension of selectivity (specificity) to the process; oligonucleotide probe binding will initially discriminate against non-target nucleic acid but some binding to non-target sequences may be expected. If the probe itself were labelled prior to binding, then further discrimination would not be possible.

The present invention, on the other hand, adds a step of selectively (sequence-specifically) incorporating a label, in the presence of the target nucleotide sequence, into the oligonucleotide probe. This selectivity may be achieved, for example, by incorporation of the label only when the target nucleotide sequence is present, or by incorporating the label in a selective or discriminating manner such that the target nucleotide sequence may be discriminated, or both.

Conveniently, selective labelling may be achieved using labelled nucleotides ie. by incorporating (or not incorporating) into the oligonucleotide probe a nucleotide carrying a label. In other words selective labelling may occur by chain extension of the oligonucleotide probe using a polymerase enzyme which incorporates a labelled nucleotide. In the case of an RNA target, the polymerase will be a reverse transcriptase enzyme. Conditions for chain extension (ie. base incorporation) and suitable polymerase enzymes are well known in the art and widely described in the literature.

Selective labelling of the oligonucleotide is preferably achieved by incorporation of a labelled dideoxynucleotide.

The term dideoxynucleotide as used herein includes all 2'-deoxynucleotides in which the 3'-hydroxyl group is absent or modified and thus, while able to be added to the oligonucleotide probe in the presence of a polymerase, is unable to enter into a subsequent polymerisation reaction. This means that only one base can be added to the probe.

Chain termination in this manner allows the reaction to be controlled, and the assay to be quantitated, if desired (see later).

Advantageously, as described above, the present invention involves chain extension of the oligonucleotide probe to incorporate a label. The present invention permits selective labelling to be achieved both by incorporation of a labelled nucleotide in a selective manner, (ie. discriminating on the basis of the label, either its presence or absence, or by selective detection of a particular label) or by nucleotide incorporation in a selective manner such that incorporation of a nucleotide (whether labelled or not) occurs only in the presence of the target nucleotide sequence (or more accurately, that the efficiency of incorporation is much reduced where the target nucleotide sequence is not present) (ie. discriminating on the basis of nucleotide incorporation or non-incorporation), or both.

As an example of such a method, if the target sequence is a key differentiating base, e.g. if the base in the nucleic acid molecule immediately adjacent to the target region to which the probe binds, is a cytosine residue, then labelled dideoxyguanine triphosphate (ddGTP) would be added to the reaction mixture for incorporation. If the probe had bound to nucleic acid at a non-target sequence, then it is unlikely that the next nucleotide is the same as the key base, and the labelled ddGTP is then unlikely to be incorporated in the oligonucleotide ie. incorporation of the oligonucleotide takes place only (or largely or substantially only) in the presence of target. The above method of differentiation applies *mutatis mutandis* if the key base is guanine, adenine, thymine or uracil.

In order further to reduce the likelihood of misincorporation of the labelled dideoxynucleotide, unlabelled dideoxynucleotide triphosphates may also be added to the reaction mixture. Using the above example, where labelled ddGTP is added, unlabelled ddCTP, ddATP and ddTTP would be added (where the target nucleic acid molecule is DNA). If only one ddNTP is present, then despite the rules of base pairing, there may be a risk that it will be incorporated where the key base is not its natural base pair, albeit at a low frequency. This may cause a background or noise signal in the assay. The inclusion of the other ddNTPs means that these will be incorporated preferentially, according to the normal rules of base pairing (C-G and A-T/U), and misincorporation of the labelled ddNTP is significantly reduced. The use of unlabelled ddNTPs thus comprises a preferred embodiment of the present invention.

In a further preferred embodiment of the present invention, selectivity of the labelling reaction is further increased by incorporation of mismatches immediately upstream of the key base. Thus, the oligonucleotide probe is designed with a mismatch or mismatches at the 3'-end to non-target nucleotide sequences, and the presence of the mismatch(es) will reduce the likelihood of oligonucleotide extension. Therefore, even if the next base after the end of the bound oligonucleotide is by chance the same as the key base, in non-target sequences incorporation of the labelled ddNTP will be reduced where there is preceding mismatch between the probe and the nucleic acid to which it has bound.

A large number of suitable labels and labelling methods are known in the art and described in the literature. Any detectable or signal-generating label or reporter molecule may be used. Convenient labels include calorimetric, chemiluminescent, chromogenic, radioactive and fluorescent labels, but enzymic or antibody-based labelling methods or signal-generating systems may also be used. Thus the term "label" as used herein includes not only directly detectable signal-giving moieties, but also any moiety which generates a signal or takes part in a signal generating reaction. Fluorescein or other fluorescently labelled ddNTPs are particularly suitable, which allow detection directly by fluorescence or indirectly by antibody interactions. These are commercially available from e.g. NEN/Dupont. ddNTPs can be labelled by e.g. [$^{35}$S], [$^{3}$H] or $^{32}$p] as described in Syvänen, A. C. et al. Genomics 8, [1990], 684–692.

In order to enhance sensitivity, more than one labelling step may be performed. In other words, the selective labelling step may be repeated one or more times, ie. performed cyclically. Increasing the number of cycles increases the sensitivity, and also when the assay is performed quantitatively (see below), the quantitative range of the method, by improving the label saturation of the probes. In order to facilitate cyclic labelling, a thermostable polymerase enzyme may be used in the label-incorporation step. Conveniently, the number of cycles of the selective labelling step may be from 1 to 50, e.g. 10 to 30 but this may be varied according to choice. An appropriate or convenient number of cycles for a given system may be determined by routine experiments.

Minisequencing methods to detect multiple single-nucleotide polymorphisms are known which involve single-nucleotide extension reactions with fluorescently labelled dideoxynucleotides (Pastinen, T. et al. Clinical Chemistry (1996) Vol. 42, 9, 1391–1397). In this case, the minisequencing reaction products were analysed by gel electrophoresis. In contrast, the present method involves a hybridisation reaction between the labelled oligonucleotide and its complementary nucleic acid sequence prior to detection and analysis.

Thus, following the selective labelling step(s), the labelled oligonucleotide probe is hybridised to a complementary nucleotide sequence. Generally, this involves separation of the labelled oligonucleotide probe from the previous reaction mixture. Label incorporation by incorporation of a labelled nucleotide, results in the so-labelled oligonucleotide probe hybridised to the target nucleic acid molecule. Strand separation to separate the probe may be achieved using denaturation methods conventional in the art e.g. high temperature heating, treatment with high pH (alkali) etc. Step (c), hybridisation to a sequence complementary to the probe, may then take place. This "complementary sequence" according to the invention may be any nucleotide sequence containing or comprising a region of absolute or substantial complementarity to the probe such that binding of the probe to the "complementary sequence" can occur. The complementary sequence may be DNA or a modification thereof such as PNA. Conveniently, the complementary sequence may take the form of the complement of the probe (ie. a sequence fully complementary to the probe). It will be understood however, that this is not absolutely essential and that the "complement" may be contained in a longer sequence, may be partial or truncated, and/or may contain sequence variation (ie. less than perfect complementarity) as long as binding of the probe to the "complementary sequence" may still occur.

In a preferred embodiment, the complementary sequence is immobilised on a solid support. Suitable immobilising supports to which the complements can be attached are known in the art and include any of the well known supports or matrices which are currently widely used or proposed for immobilisation, separation etc. These may take the form of particles, sheets, gels, filters, membranes, fibres, capillaries, chips or microtitre strips, tubes, plates or wells etc. Methods of immobilising or attaching oligonucleotides to solid supports are likewise known in the art. Particularly preferred are membrane strips (commercially available from NEN and known as GeneScreen) on to which the complementary sequences may be spotted and then U. V. cross-liked, or DNA chips (microchips, glass chips) now common in molecular biology procedures. The use of such solid supports, in particular chips which can carry an oligonucleotide array ie. a number, e.g. up to 250, of different oligonucleotides complementary to the oligonucleotide probes used in the earlier part of the assay, represents a particularly preferred embodiment of the invention.

Hybridisation step (c) permits the quantitative separation of the labelled probes. This is advantageous in the context of a quantitative assay.

Following the hybridisation step, the label on the oligonucleotide probe is detected. As mentioned above in the context of the label, the detection may be by any means known in the art, depending on the label selected. Signal amplification may also be used, if desired, as described in the art (see, for example, P. Komminoth and M. Werner, Target and Signal Amplification, approaches to increase the sensitivity of in situ hybridisation, 1997 Histochem. Cell Biol. 108:325–333). Detection may also be qualitative, or quantitative or semi-quantitative. Thus, for example, a visual e.g. calorimetric, chromogenic, fluorescent or other signal detectable from the label may be used to provide a simple yes or no indication of the presence or absence of the target nucleotide sequence. Advantageously, however, the detection is such as to yield a quantitative assessment of the amount of target nucleotide present in the sample. This may be an absolute indication of the amount of target present or some other quantitative or semi-quantitative indicator e.g. a percentage, ratio, or similar indicator, e.g. relative to total nucleic acid in the sample.

Quantitation of the target nucleotide sequence may further be correlated to a quantitation of the number of organisms or cells containing the target in question. Thus, in further aspects, the invention provides methods of determining the amount of a target nucleotide sequence or the number of cells containing a target nucleotide sequence using the nucleic acid detection assay hereinbefore described.

As mentioned above, the target nucleic acid may be any DNA or RNA molecule. It may thus be directly the nucleic acid of a target cell or organism. It may be desirable, however, to amplify the nucleic acid prior to detection using the assay method of the invention and advantageously the target nucleic acid may thus be an amplicon of an in vitro amplification reaction. Amplification may however also take place by other means including in vivo cloning methods. Any method of in vitro amplification may be used, including both linear and exponential methods. Representative methods thus include PCR, NASBA and ligase chain reaction. Due to its convenience, PCR and its variants will commonly be the method of choice.

In the context of a quantitative assay, a quantitative in vitro amplification method may be combined with the detection assay of the invention. In particular, in a preferred embodiment of the methods of the present invention, the oligonucleotide probe binding step is preceded by a competitive PCR reaction. A variety of methods of competitive PCR exist and are described in the literature. Any of the known techniques may be used. (For a review see e.g. Srebert, P. D. and Larrick, J. W. [1992] Nature, 3, 557–558).

In such a method, nucleic acid incorporating the target nucleotide sequence is co-amplified with a selected competitor molecule containing the same primer template sequences as the target molecule and thus the competitor competes with the target for PCR primer binding and amplification. The competitor comprises a means for differentiating from the target, conveniently a recognition sequence for binding to a competitor-specific oligonucleotide probe, analogous to the "target-specific" oligonucleotide probe described in the context of the detection assay above (ie. the probe of step (a) above). The recognition sequence is thus analogous to the "target region" of the oligonucleotide probe above. A single known amount of competitor may be added, for comparison to a standard curve, or a series of amplifications may be performed using varying amounts of competitor e.g. a dilution series. Primers complementary to sequences flanking the target nucleotide sequence in the nucleic acid molecule of interest (and to the same sequences in the competitor) are added and PCR amplification is performed. Competitive PCR enables the detection to be performed with a built in reference to provide more accurate analysis of the results. A standard curve may be constructed using standard techniques conventional in the art.

Figure 1:
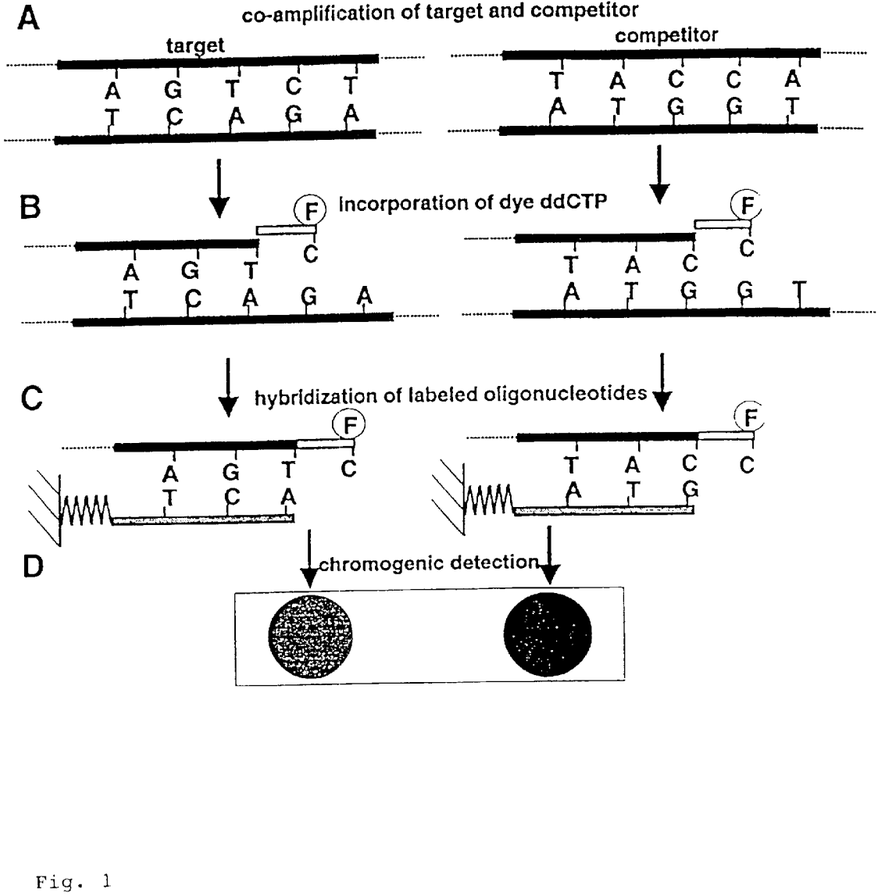
FIG. 1 is a schematic representation of the quantitative labelling assay. A known concentration of competitor DNA was added to the purified target and co-amplified with the same primer pair (A). Two oligonucleotides, one complementary to an internal segment of the competitor and one complementary to an internal segment of the target were sequence specifically extended by a fluorescein labelled dideoxy cytosine by thermo-cycling (B). The labelled primers were then hybridized to their immobilized complements (C). Finally, a chromogenic detection of the label was performed (D), and the relative signal intensities determined.

In such a competitive PCR step, amplicons are produced deriving from both target and competitor DNA. The competitor amplicon is subjected to a detection assay procedure in an analogous manner to the target amplicon, as described above. The amplified competitor sequence includes a known recognition sequence which behaves in the same way as the target region in the target nucleic acid molecule under detection. For example, an oligonucleotide probe binding selectively to this recognition region of the competitor is added to the reaction mixture at the same time as the probe to the target region of the target molecule is added, both oligonucleotides being designed to be single base extended with a labelled ddNTP when bound to their respective target sequences. A complementary sequence to the competitor oligonucleotide probe which has been labelled following binding to the competitor is also provided, preferably immobilised, and the labelled oligonucleotide probe hybridises to this complementary sequence before detection. The labels of the target and competitor oligonucleotides can then be detected and, in particular, the relative strengths of the measured signal used to evaluate the amount of target nucleic acid which was present in the original sample given the known amount of competitor added to the system. This aspect of the invention is represented in FIG. 1. It is not necessary that the label for the competitor and the target sequence are different, indeed they are preferably the same. Differentiation between competitor and target, as between a plurality of different target sequences, is preferably achieved spatially; the position of the complementary sequence to each oligonucleotide probe on e.g. the microchip array is known and the strength of signal at each position is measured.

Titration experiments can be used to determine the optimum amount of competitor to be used in any particular assay, as described in the following Examples. The amount of competitor selected preferably allows detection of a low frequency of target nucleic acid molecules and reproducible amplifications. Suitable concentrations may vary from $6 \times 10^{-8}$ to $6 \times 10^{-10}$ pmol, preferably from $4 \times 10^{-9}$ to $8 \times 10^{-9}$ pmol.

Preferably, sufficient cycles of PCR are performed so that a saturation level is achieved; in that way the amplified DNA contains substantially the same ratio of target DNA to competitor DNA as that present before PCR.

It is advantageous to provide conditions such that the competitor and target DNA are amplified equally efficiently by PCR and it is therefore desirable that the size and GC-content of each fragment is kept substantially the same. In some instances it will also be necessary to take into account the efficiency of the cell lysis of the sample which can make some of the genomic DNA less available for the PCR. In addition, the target DNA may be part of chromosomal DNA in the initial cycles, while the competitor DNA may be, for example, in the form of a small plasmid. Thus it might be necessary to adjust for the relative amplification efficiencies of these early PCR cycles.

Alternative amplification strategies may also be used in this aspect of the invention, for example NASBA and ligase chain reaction.

Any suitable polymerase may be used, although it is preferred to use a thermophilic enzyme such as Taq polymerase to permit the repeated temperature cycling without having to add further polymerase, e.g. Klenow fragment, in each cycle.

As mentioned above, the target nucleic acid may be cDNA synthesised from mRNA in the sample, and the method of the invention is thus applicable to diagnosis on the basis of characteristic mRNA. Such preliminary synthesis can be carried out by a preliminary treatment with a reverse transcriptase, conveniently in the same system of buffers and bases to be used in the subsequent amplification (e.g. PCR) steps. Since the PCR procedure requires heating to effect strand separation, the reverse transcriptase will be inactivated in the first PCR cycle. When mRNA is the target nucleic acid, it may be advantageous to submit the initial sample, to treatment with an immobilized polydT oligonucleotide in order to retrieve all mRNA via the terminal polyA sequences thereof. Alternatively, a specific oligonucleotide sequence may be used to retrieve the RNA via a specific RNA sequence. The oligonucleotide can then serve as a primer for cDNA synthesis, as described in International Patent Application WO-A-90/11446.

The PCR (or other in vitro) amplification of target and competitor nucleic acid provides a first level of specificity but a low level of non-target/non-competitor molecules may be amplified in this reaction, hence the selective labelling of the oligonucleotide probes based on signature sequences in the target and the competitor amplicons according to the present invention. The quantification is based on the signal ratio of target to competitor alone and is not affected by any non-target/non-competitor molecules which may have been amplified in the first reaction.

When the main detection assay follows a PCR or other in vitro amplification step based on chain extension, then it is necessary to separate the dNTPs from the previous reaction e.g. in the PCR product or to inactivate them to ensure that they could not be involved in subsequent elongation of the oligonucleotides bound to target/competitor nucleic acid in place of the terminating ddNTPs. Physical separation of the dNTPs from the PCR product is possible by e.g. gel electrophoresis, precipitation, affinity purification, chromatography or filtration. However it is preferred to inactivate the dNTPs by removing the reactive phosphate groups by a phosphatase so that the nucleotides can no longer be used for significant chain elongation.

Target nucleic acid for use in the method of the invention may be obtained or prepared by any convenient technique in the art. Many different methods for isolating nucleic acids from cells and organisms are described in the literature and any of these could be used.

For example, methods for the extraction of nucleic acid from environmental samples are described by Bowman, J. P. and Sayler, G. S. in Molecular Approaches to Environmental Microbiology (1996), pp 63–97. However, a particularly preferred embodiment of the present invention combines a detection method as described above with the solid-phase method for combined cell and nucleic acid isolation described by us in Rudi et al., Appl. Environ. Microbiol. (1998), 64(1), pp 34–77.

The method of isolating nucleic acid from a sample of cells which is described in this paper comprises:

(a) binding cells in the sample to a solid support to isolate the cells from the sample;

(b) lysing the isolated cells; and (c) binding nucleic acid released from said lysed cells to said same solid support.

The bound nucleic acid may be used directly in a detection assay of the invention or it may be released from the support.

The detection assay of the present invention may advantageously find application in any procedure where it is desired to detect nucleic acids, for example in any procedure relying on DNA or RNA identification, e.g. diagnosis, detection of infections or contaminating organisms or pathogens, clinical monitoring, forensics, food and environmental safety and monitoring, or for distinguishing between different cells or cell types, mutation detection, analysis of polymorphisms, e.g. in tissue typing etc. and as a general molecular biology tool. The complete nucleic acid-based assay comprising sample preparation, DNA amplification, selective labelling and detection is of particular benefit in quantifying the amount of toxin-producing cyanobacteria in water sources. This combined isolation and detection method comprises a particularly preferred embodiment of the present invention. The assay provides a lower detection limit of 200, preferably 100 cells/ml (of a particular cyanobacteria against a background of $10^5$ cells/ml of other cyanobacteria) and a quantitative range of more than three orders of magnitude. The methods described in principle above and in more detail below are suited for automation, providing the means for the development of high throughput systems for routine environmental monitoring.

For example, water-blooms formed by cyanobacteria have a relatively high frequency of toxicity (between 25 and 70%), and constitute a potential health hazard to livestock and humans. This is particularly the case for blooms of cyanobacteria belonging to the genus Microcystis. Species of this genus can produce several toxins, with the hepatotoxic microsystins being the most potent. It would therefore be desirable if a method could be developed which provided a reliable, quick and convenient way to detect and quantify these bacteria.

The methods of the invention are particularly suitable in this respect, in that by selection of oligonucleotides to signature sequences within the genome of different bacteria of interest, a single sample can be analysed in one procedure for several different microorganisms. Signature sequences for distinct bacterial groups are widely known and published in the literature, for cyanobacteria a classification system based on 16S rDNA sequence information can be used (see e.g. J. R. Marchesi, T. Sato, A. J. Weightman, T. A. Martin, J. C. Fry, S. J. Hiom, and W. G. Wade, 1998. Design and evaluation of useful bacterium-specific PCR primers that amplify genes coding for bacterial 16S rRNA. *Appl. Environ. Microbiol.* 64:795–799: Turner, S. (1998) Origins of algae and their plastids, pp 13–53 Ed. Bhattacharya, D. NY: Springer-Verlag and Giovanni, S. J., Turner, S., Olsen, G. J., Barns, S., Lane, D. J. and Pace, N. R. (1988) J. Bacteriol 170 pp 3584–92).

The Examples which follow describe a fully integrated assay for analysis of complex cyanobacterial communities. The methods of the invention are equally suitable for use in the investigation of other microbial communities.

Complementary sequences to the different labelled oligonucleotides can be arranged on a single microchip in a pre-determined manner to allow quantification of the levels of different bacteria, preferably by comparison of the ratio of competitor signal to the signal for each bacterial group. Such multiplex quantitative assays preferably use high density oligonucleotide arrays immobilised on glass chips, with subsequent direct detection of the fluorescein-label (see e.g. Schena, M. et al., Science, (1996) 270: 467–470; and R. J. Lipshutz, D. M. Morris, M. Chee, E. Hubbell, M. J. Kozal, N. Shah, N. Shen, R. Yang, and S. P. A. Fodor. Using oligonucleotide probe arrays to access genetic diversity, Bio Techniques 19:442–447).

The invention also comprises kits for carrying out the methods of the invention. These will normally include at least the following components:

(a) an oligonucleotide probe capable of binding to a target nucleic acid molecule containing the target nucleotide sequence (ie. directed to a target region within the nucleic acid molecule;

(b) means for selective labelling of the oligonucleotide probe; and (c) nucleotide sequences complementary to the oligonucleotide probes, preferably immobilised on a solid support.

The means for selective labelling will conveniently comprise a polymerase enzyme and at least a labelled nucleotide, preferably a labelled ddhTP, optionally with corresponding unlabelled nucleotides also present.

The above described invention will now be illustrated by the following non-limiting Examples in the field of cyanobacteria detection with reference to the drawings in which:

The assays were performed on dilution series of purified DNA. The amount of DNA is given as genomic copies (assuming a genomic copy weight of 5 fg). In panel A, 10 μl of the products from the competitive PCR reaction were loaded in each lane on a 1.5% agarose-gel (containing 30 μg/ml of ethidium bromide) and electrophoresed using 1×TBE at 100 volts for 1 hour. The products were visualized by U. V.-transillumination. The labelling assay shown in panel B was performed as described in the Examples. In panel C, the signal intensities (measured as the difference in the average pixel value in a 8 bits grayscale, between the signal and the background) for the target in panel A measured relative to the total signal intensities of both the target and the competitor (●). Respective values for the labelling assay in panel B are also shown (▲). The pictures were taken with a Cohu High Performance CCD Camera, and printed on a digital color printer (Mavigraph UP-D1500CNE. Sony, Japan).

FIG. 3—is a graph showing the percentage of the signal intensities for the target spots relative to the total signal intensities, with mean value for all the experiments, and error bars for standard deviation (3 degrees of freedom). Complete assay with $6\times10^{-9}$ pmol competitor on dilution series of *Microcystis aeruginosa* NIVA-CYA 43 in different aqueous environments. Cells were diluted in sterile water, water containing Anabaena Lemmermannii NIVA-CYA 83/1

($10^5$ cells/ml), water containing *Planktothrix agardhii* NIVA-CYA 29 ($10^5$ cells/ml) and in water from Lake Akersvatnet, Norway (sampled May 30, 1996). The complete assay including solid-phase cell concentration and DNA purification was performed as described in the Examples.

FIG. 4—(A)—shows the results of the labelling assay following solid-phase cell concentration and DNA purification as described in the Examples. Complete assay with $6 \times 10^{-8}$ pmol competitor on dilution series of *Microcystis aeruginosa* NIVA-CYA 43 in water from Lake Akersvatnet, Norway (sampled May 30, 1996).

(B)—is a graph showing the percentage of the signal intensities for the target spots relative to the total signal intensities. The pictures were taken with a Cohu High Performance CCD Camera, and printed on a digital color printer (Mavigraph UP-D1500CNE).

FIG. 5—(A)—shows membrane strips with probes.

(B)—shows signal intensities for the respective probes.

(C)—shows phylogenetic position for the different probes.

The probes were spotted on the membrane in the following order: first row—pKO, pAP and pMI3; second row—pMI2, pDK and pPL2; third row—pPL1, pAL and pNOS; fourth row—pUN. The strains tested are for membranes a1; *Aphanizomenon gracile* NIVA-CYA 103, a2; *Anabaena lemermannii* NIVA-CYA 266/1, a3; *Nostoc sp.* NIV-CYA 123, b1; *Phormidium sp.* NIVA-CYA 203, b2; *Planktothrix prolifica* NICA-CYA 320, b3; *Microsystis aeruginosa* NIVA-CYA 143, c1; *Microcystis flos-aquae* NIVA-CYA 144, c2; *Pseudanabaena limnetica* NIVA-CYA 276/6, and c3; Chlorobium. The signal intensities for each spot was determined. The phylogenetic position of the different strains and probes are visualised by a phylogenetic tree. The tree was built with the neighbour-joining algorithm, using Kimura distances. Each branch in the tree has a bootstrap support above 65%.

EXAMPLES

Example 1
Organisms and Sample Preparation

The organisms used are from the Norwegian Institute for Water Research. The cultivation was performed in medium Z8. The illumination was provided by fluorescent lamps exposing the strains with 30 $\mu Em^2 s^{-1}$. Two different *Microcystis aeruginosa* strains (NIVA-CYA 228/1 and 43) were used as templates in the development of the assay. The system was also tested on experimentally modified water samples collected from Lake Akersvatnet, Norway. The cells were counted by microscopy in a Fuchst-Rosenthal counting chamber (Carl Hecht, Sondheim, Germany).

DNA was either purified with a standard phenol/chloroform protocol from cell pellets of unialgal cultures, or by a solid-phase cell concentration and DNA purification protocol (Rudi, K., Larsen F. and Jakobsen, K. J. in Applied and Environmental Microbiology, (1998), 64, Vol. 1, pp 34–37). In the solid-phase protocol, cells of cyanobacteria from 1 ml aqueous solution were adsorbed for 20 minutes onto paramagnetic beads (final volume 2 ml) in a buffer containing 50% isopropanol, 0.75 M ammonium acetate and lU (the beads in 200 $\mu$l lysis buffer) Dynabeads DNA DIRECT (Dynal A/S, Oslo, Norway). The magnetic beads and the adsorbed bacteria were attracted to the side of a 2 ml microcentrifuge tube by a MPC-Q magnet (Dynal A/S). Then 20 $\mu$l of 4 M guanidine thiocyanate-1% Sarkosyl was added, and the incubation continued at 65° C. for 10 minutes. The DNA was precipitated onto the beads by addition of 40 $\mu$l 96% ethanol, with subsequent incubation at room temperature for 5 minutes. Finally, the DNA and bead complex was washed twice with 500 $\mu$l 70% ethanol using the magnet between each washing. To remove residual ethanol the complex was dried at 65° C. for 5 minutes. The complete bead and DNA complex was then used in the amplification reactions.

Competitive PCR (Schematically Shown in FIG. 1A)

For selective amplification of genomic DNA from Microcystis we used the 16S rDNA primers 5'-AGCCAAGTCTG CCGTCAAATCA-3' (CH) and 5'-ACCGCTACACTGGGAATTCCTG-3,(CI) (Rudi, K. et al. in Appl. Environ. Microbiol. 63, 2593–2599). The competitor 5'AGCCAAGTCTGCCGTCAAATCAAGCTG CCTCACTGCGGAGCTCGGACCAGGAATTCCCAG TGTAGCGGT-3' is an oligonucleotide with sequences complementary to the PCR primers CH—CI, and the primer DK (see below) used in the cyclic labelling reaction. Amplification reactions using the GeneAmp 2400 PCR thermocycler (Perkin Elmer, Norwalk, Conn.) contained 10 pmol primers, $6 \times 10^{-9}$ pmol competitor, 200 $\mu$M of each deoxynucleotide triphosphate, 10 mM Tris-HCl (pH 8.8), 1.5 mM $MgCl_2$, 50 mM KCl, 0.1% Triton X-100, 1U of DynaZyme DNA polymerase (Finnzymes Oy, Espoo, Finland) and purified DNA in a final volume of 50 $\mu$l. Prior to amplification, the DNA was denatured for 4 minutes at 94° C. and after amplification an extension step for 7 minutes at 72° C. was included. The cycling was done for 40 cycles using the parameters; 94° C. for 30 seconds, 58° C. for 30 seconds and 72° C. for 30 seconds.

Cyclic Labelling (Schematically Shown in FIG. 1B)

Five $\mu$l of the PCR products from the competitive reaction were used in the cyclic labelling reaction. The deoxynucleotide triphosphates were dephosphorylated by addition of 100 nm Tris-HCl (pH 8.0), 50 nm $MgCl_2$ and lU shrimp alkaline phosphatase (USB, Cleveland, OH), with subsequent incubation at 37° C. for 1 hour. Finally, the phosphatase was inactivated by heating at 96° C. for 10 minutes.

The cyclic labelling reactions were carried out in 20 $\mu$l volumes containing; 3 pmol primer 5'-GTCCGAGCTCCGCAGTGAGGCAG-3' (DK) complementary to the competitor. 3 pmol primer 5'-TCTGCCAGTTTCCACCGCCTTTAGGT-3' (DB) complementary to the Microcystis amplicon, 10 pmol ddATP, 10 pmol ddGTP, 10 pmol ddTTP (Boehringer GmbH, Mannheim, Germany), 7 pmol fluorescein-12-ddCTP (NEN, Boston, Mass.), 1.25 $\mu$l Thermo Sequenase reaction buffer, 1.1 $\mu$l enzyme dilution buffer, 0.15 $\mu$l Thermo Sequenase (Amersham International plc, Buckinghamshire, England) and 6 $\mu$l phosphatase-treated PCR product. The labelling was done for 25 cycles using the parameters; 95° C. for 30 seconds and 50° C. for 4 minutes.

Hybridization and Chromogenic Detection (Schematically Shown in FIGS. 1C and D)

One $\mu$l (100 pmol/$\mu$l) of primer 5'-ACCTAAAGGCGGTGGAAACTGGCAGA-3' (DA) and 5'-CTGCCTCACTGCGGAGCTCGGAC-3' (DJ) were spotted onto membrane strips (0.4×2 cm) GeneScreen (NEN), and then U. V. cross-linked with 5000 joule/cm$^2$. Primer DA is complementary to primer DB, and primer DJ is complementary to primer DK. The strips were prehybridized for 2 hours at 37° C. in a prehybridization solution containing 0.7×SSC, 1×SPEP, 5×Denhardts and 100 µg/ml heterologous DNA. The products from the cyclic labelling reactions were added to 0.5 ml hybridization solution (0.7× SSC, 1×SPEP, 1×Denhardts, 10% Dextran sulfate and 100 µg/ml heterologous DNA) in a 2 ml microcentrifuge tube, and denatured at 95° C. for 5 minutes. The strips were added, and the incubation continued with gentle inversion for 2 hours at 37° C. The membrane strips were washed in 50 ml (1×SSC and 1% SDS), then in 50 ml (0.1×SSC and 0.1% SDS), and finally twice in 50 ml (0.10 M Tris-HCl [pH 7.5] and 0.15 M NaCl). Each washing was performed by brief vortexing at room temperature.

For antibody detection the membrane strips were blocked with 20 ml (0.10 M Tris-HCl [pH 7.5], 0.15 M NaCl and 0.5% skimmed milk) for 1 hour and incubated in 10 ml of the same buffer containing 1/1000 of Antifluorescein-HRP Conjugate (NEN) for an additional 1 hour. The membrane strips were washed 3 times by brief vortexing in 50 ml (0.10 M Tris-HCl [pH 7.5] and 0.15 M NaCl). The chromogenic reaction was done with the RENAISSANCE 4CN Plus For Chromogenic Detection of HRP for 5 minutes, according to the manufacturers recommendations (NEN).

The relative signal strengths were measured using a CCD video camera (Cohu High Performance CCD Camera, Japan), and analyzed using the Gel-Pro ANALYZER software (Media Cybernetics, Silver Spring, Md.).

Detection assay on defined samples containing purified DNA. By titration experiments the optimum amount of competitor (both for obtaining low detection limits, and for reproducible amplifications) was found to be $6 \times 10^{-9}$ pmol (i.e. 3600 molecules) per sample test. Accordingly, $6 \times 10^{-9}$ pmol competitor was used in the testing of the assay on purified DNA from *Microcystis aeruginosa* NIVA-CYA 43. Dilution series of Microcystis DNA from approximately $10^7$ to $10^0$ genomic copies (assuming a genome size of 5±3 Mb (9b)) were used in both the competitive PCR assay (FIG. 2A), and in the subsequent labelling assay (FIG. 2B).

Figure 2:
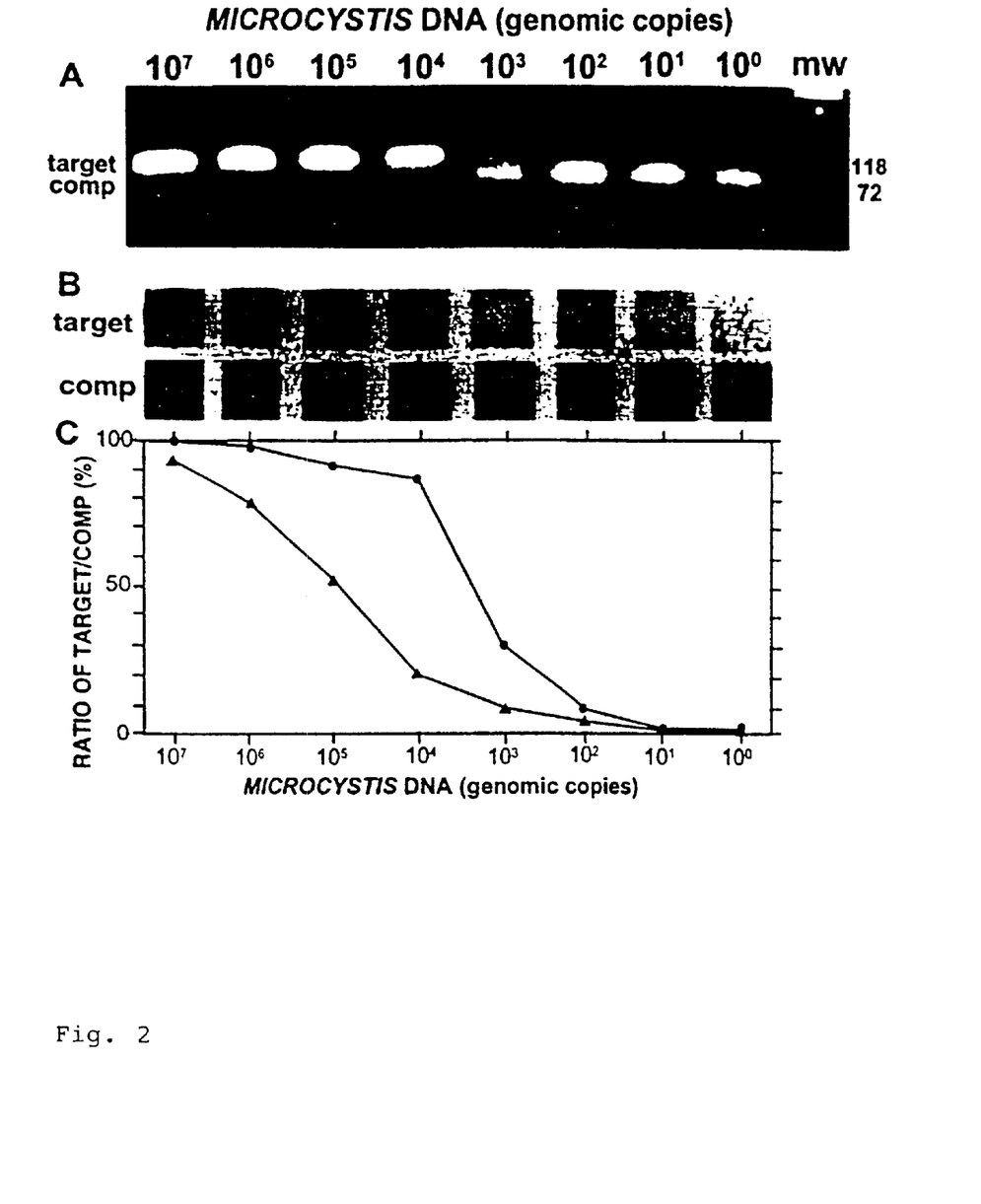
FIG. 2 (A)—shows gel results from a competitive PCR on dilution series of DNA isolated from Microcystis aeruginosa NIVA-CYA 43, (B)—shows the results of the labelling assay, (C)—is a graph showing the intensities of the target signals relative to the total signal intensities.

Measurements of the ratio between target relative to competitor products, as determined by agarose gel electrophoresis, gave a quantitative range from $10^5$ to $10^2$ genomic copies (FIG. 2C). In contrast, the labelling assay the subject of the present invention gave a quantitative range of from more than $10^7$ down to $10^2$ genomic copies. This is approximately a 100-fold increase in dynamic range compared to agarose gel electrophoresis detection assays (FIG. 2C). As few as 10 copies could be detected for the labelling assay by increasing the incubation time of the chromogenic detection reaction from 5 to 30 minutes. Live video capture of the chromogenic detection reaction may be used to give a quantitative range down to this level. That is, time-curves from 0 to 30 minutes for the colour density of the target and competitor spots can be used to extrapolate the relative signal intensities, although the competitor spot is colour-density saturated after 30 minutes.

Effect on the quantitative range by the number of cycles in the labelling reaction. The cyclic labelling reaction increased the quantitative range of the assay compared to direct detection of the amplified DNA. For competitive PCR—using a logarithmic scale for the target concentration—the ratio of competitor and target signals resulted in a sigmoid curve with relatively narrow quantitative range (see FIG. 2C). A sigmoid curve was also obtained by performing the cyclic labelling assay with just a few labelling cycles. However, by increasing the number of labelling cycles, the competitor or the target oligonucleotides were label saturated (all the probes were labelled) at each of the dilution series endpoints, respectively, leading to curve with a wider quantitative range (see FIG. 2C). Increasing the cycle number further resulted in a curve which was flatter in the middle because of label saturation of both oligonucleotides at this location.

Quantification of Microcystis in water samples. The complete quantitative assay which includes the solid-phase cell concentration and DNA purification method was carried out on dilution series ($10^5$–$10^0$ cells/ml) of *Microcystis aeruginosa* (strains NIVA-CYA 43 and 228/1). *Planktothrix agardhii* NIVA-CYA 29 (filamentous) and *Anabaena lemmermanii* NIVA-CYA 83/1 (filamentous and heterocyst containing) were used as controls of the reaction specificity. Microcystis cultures were diluted in pure water, water containing $10^5$ cells/ml of *Planktothrix agardhii* NIVA-CYA 29, water containing $10^5$ cells/ml of *Anabaena lemmermanii* NIVA-CYA 83/1, and water sampled from Lake Akersvatnet, Norway.

Figure 3:
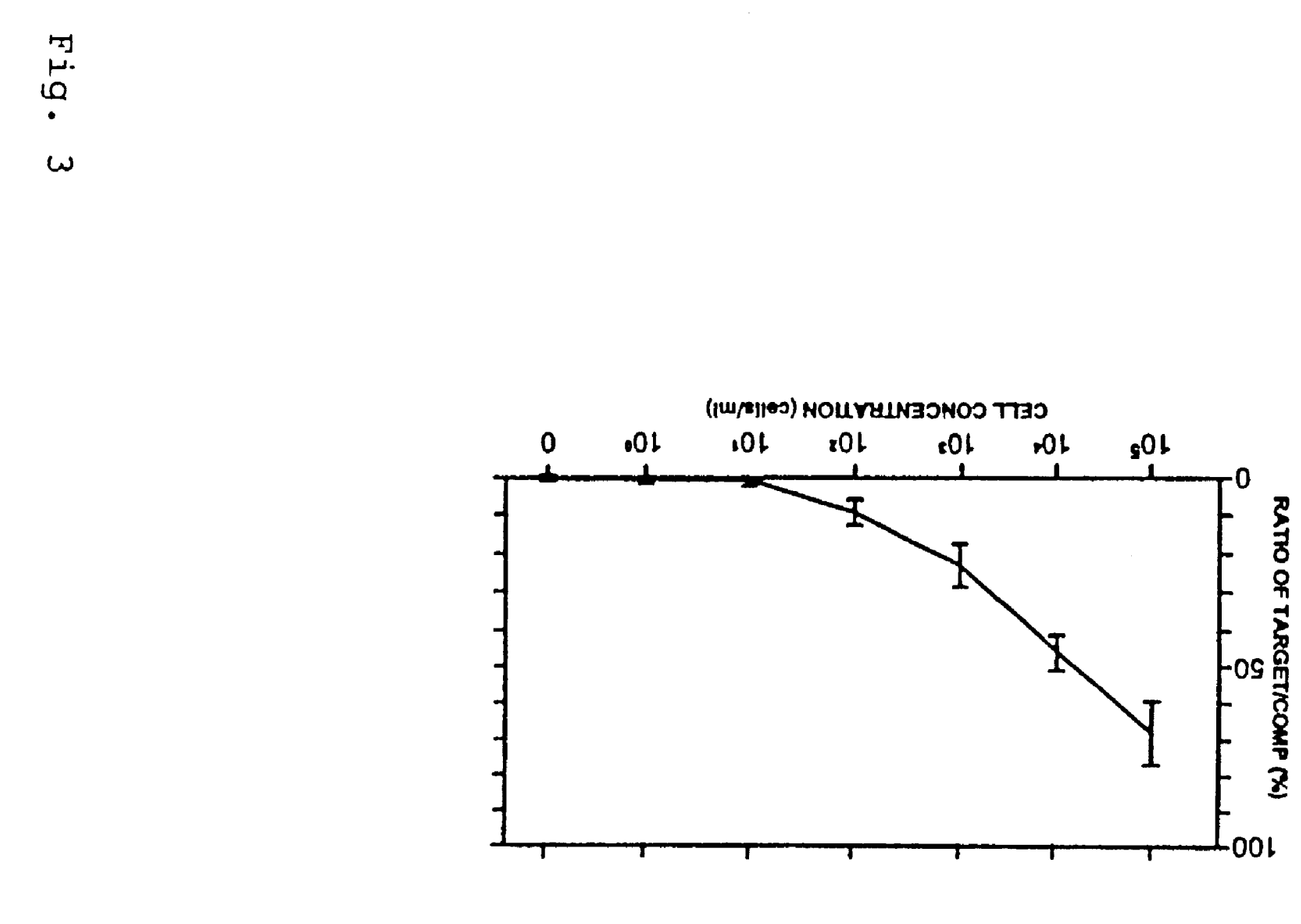

There were no significant differences in either specificity or sensitivity of the assay for the different conditions tested. With $6 \times 10^{-9}$ pmol competitor we obtained a quantitative range spanning from more than $10^5$ down to $10^2$ cells/ml in all cases (results for *Microcystis aeruginosa* NIVA-CYA 43 are shown in FIG. 3). By lengthening the incubation time for the chromogenic detection reaction from 5 to 30 minutes we could detect down to 10 cells/ml.

The detection curve for the complete detection assay (including solid-phase cell concentration and DNA purification) has about the same slope as the curve obtained for the dilution series of purified DNA (compare FIGS. 2C and 3), indicating that the cell concentration and DNA purification (sample preparation) method is not affected by the sample composition. Furthermore, these results also show that the solid-phase cell concentration and DNA purification method can be used for quantitative analysis directly from water-samples.

Figure 4:
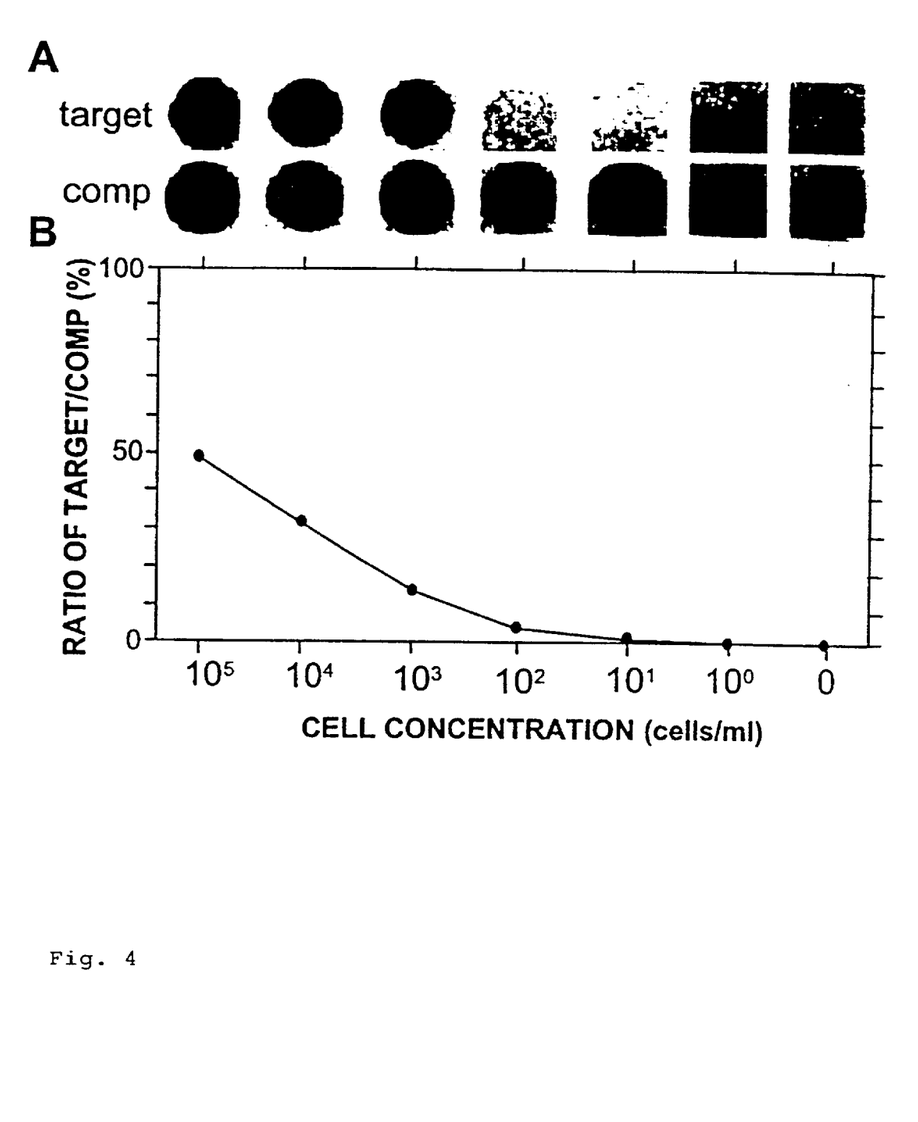

The detection limit was dependent on the amount of competitor used, with a lower limit ($6 \times 10^{-9}$ pmol) competitor. Increasing the amount of competitor 10-fold ($6 \times 10^{-8}$ pmol) also resulted in about 10-fold increased detection limit (FIG. 4). However, lowering the amount to $6 \times 10^{-10}$ pmol gave irreproducible results. Thus, we conclude that $6 \times 10^{-9}$ pmol was also the optimum amount of competitor both for obtaining low detection limits and reproducible detections for the complete assay on water-samples.

Complete assay for quantification of cyanobacteria in water. Cyanobacteria belonging to the genus Microcystis can produce several different types of toxins, with the hepatotoxic microcystins as the most potent. This toxin not only causes an acute poisoning by liver damage, but can also be a carcinogenic tumor promoter on long term exposure to low doses. Thus, a continuous monitoring system to screen for the presence of the organisms producing this toxin is important.

Health authorities in Australia (New South Wales Bluegreen Algae Task Force, 1992) have already adopted a three-level alert system based on cyanobacterial cell counts in water. Level 1 is 500–2000 cells/ml, at this level water authorities are alerted and water sampling for monitoring is increased. Level 2 is 2000–15000 cells/ ml, at this point toxicity testing is carried out. Level 3 is above 15.000 cells/ml, if activated carbon is not available then the water may be declared unsafe for human consumption. With a detection limit for Microcystis of 100 cells/ml and a quantitative range of more than three orders of magnitude, the methods of the invention described herein are suited for the monitoring of both low Microcystis concentrations and the detection of potential toxic waterblooms in drinking water.

Development of multiplex assays. The general sample preparation with the solid-phase cell concentration and DNA purification method, combined with the specificity in the detection method, enable multiplex determinations. Using competitive PCR, multiple targets may be quantified by using e.g. universal 16S rDNA primers in the competitive reaction. Then, different oligonucleotide probes can be labelled based on signature sequences for distinct bacterial groups, and finally, the ratios of the competitor signal can be compared to the signals for each of the bacterial groups.

Example 2

Unlike traditional classification based on morphology/cytology, classification based on nucleic acid sequences reflect the evolution and phylogeny of the organisms. 16S rDNA-targeted probes were constructed to detect the major cyanobacterial groups Microcystis, Planktothrix, Anabaena and Aphanizomenon. Probes were also constructed to differentiate groups of different phylogenetic depth. A probe was constructed to detect the Nostoc group (which includes Anabaena and Aphanizomenon), and one probe was constructed to detect all eubacteria (including chloroplasts). The specificity of the constructed probes was tested on unialgal cultures. This information was subsequently used to determine the relative distribution and abundance of the targeted organisms in 7 lake communites.

Organism and Sample Preparation.

The following unialgal cultures from the Norwegian Institute for Water Research was used; Aphanizomenon gracile NIVA-CYA 103, *Anabaena lemmermannii* NIVA-CYA 266/1, Nostoc sp. NIVA-CYA 124, Phormidium sp. NIVA-CYA 203, *Planktothrix prolifica* NIVA-CYA 320, *Microrystis aeruginosa* NIVA-CYA 143, Microcystis flos-aquae NIVA-CYA 144, *Pseudanabaena limnetica* NIVA-CYA 276/6. The cultivation was performed in medium Z8 [Norwegian-institute-for-water-research, Oslo (1990) Culture Collection of algae, catalogue of strains]. The illumination was provided by fluorescent lamps exposing the strains with 30 $\mu Em^{-2}s-1$. Aliquots of dense cultures (1 ml containining approximately $10^7$cells/ml) were pelleted in a microcentrifuge at 5,000 rpm for 10 min and immediately frozen at −80° C. The DNA was purified from the frozen pellets with the magnetic bead-based DNA Direct DNA isolation Kit (Dynal A/S, Oslo, Norway), using a protocol modified for the purification from cyanobacteria [Rudi K., Kroken, M., Dahlberg, O. J., Deggerdal, A., Jakobsen, K. S. and Larsen, F. (1997) Biotechniques 22, 506–11].

The samples collected from the field were immediately conserved in isopropanol, as described for the cell concentration step below. The samples were then transported to the laboratory, and processed further. The DNA was purified by a solid-phase cell concentration and DNA purification protocol previously developed by Rudi et at. (1998). In the solid-phase protocol, cells from 0.8 ml aqueous solution were adsorbed for 20 min onto paramagnetic beads (final volume 2 ml) i n a buffer containing 50% isopropanol, 0.75 M ammonium acetate and IU (the beads in 200 $\mu$l lysis buffer) Dynabeads DNA DIRECT (Dynal A/S, Oslo, Norway). The magnetic beads and the adsorbed bacteria were attracted to the side of a 2 ml microcentrifuge tube by a MPC-Q magnet (Dynal A/S). Then 20 $\mu$l 4 M guanidine thiocyanate-1% Sarkosyl was added, and the incubation continued at 65° C. for 10 min. The DNA was precipitated onto the beads by addition of 40 $\mu$l 96% ethanol, with subsequent incubation at room-temperature for 5 min. Finally, the DNA and bead complex was washed twice with 500 $\mu$l 70% ethanol using the magnet between each washing. To remove residual ethanol the complex was dried at 65° C. for 5 min. The complete bead and DNA complex was then used in the amplification reactions.

PCR Amplfication.

Ribosomal DNA was amplified, using the universal primer set CC—CD. Amplification reactions using the GeneAmp 2400 PCR thermocycler (Perkin Elmer, Norway, Conn.) contained 10 pmol primers, 200 $\mu$m of each deoxynuclewtide triphosphate, 10 mM Tris-HCl (pH 8.8), 1.5 mM $MgCl_2$, 50 mM KCl, 0.1% Triton X-100, 1U of DynaZyme DNA polymerase (Finnzymes Oy, Espoo, Finland) and purified DNA in a final volume of 50 $\mu$l. Prior to amplification, the DNA was denatured for 4 min at 94° C. and after amplification an extension step for 7 min at 72° C. was included. The cycling was done for 35 cycles using the parameters; 96° C. for 15 s, 70° C. for 30 s and 72° C. for 1 min.

Cyclic Labelling.

Twenty $\mu$l of the PCR products from the amplification reactions were used in the cyclic labeling reaction. The deoxynucleotide triphosphates were dephosphorylated by addition of 100 nm Tris-HCl (pH 8.0), 50 nm $MgCl_2$ and 1 U shrimp alkaline phosphatase (USB, Cleveland, OH), with subsequent incubation at 37° C. for 1 hour. Finally, the phosphatase was inactivated by heating at 96° C. for 10 min.

The cyclic labeling reactions were carried out in 80 $\mu$l volumes containing 3 pmol of each of the primers in Table 1 below, 10 pmol ddATP, 10 pmol ddGTP, 10 pmol ddTTP (Boehringer GmbH, Mannheim, Germany), 7 pmol fluorescein-12-ddCTP (NEN, Boston, Mass.), 1.25 $\mu$l Thermo Sequenase reaction buffer, 1.1 $\mu$l enzyme dilution buffer, 0.15 $\mu$l 32 U/$\mu$l Thermo Sequenase (Amersham Pharmacia plc, Buckinghamshire, England) and 25 $\mu$l phosphatase-treated PCR product. The labeling was done for 10 cycles using the parameters; 95° C. for 30 sec and 50° C. for 4 min.

TABLE 1

| Probes | Oligonucleotide probes probe sequences[1] |
|---|---|
| pKO | 5'CCTCTGGTACCGTCAGGTTGCTTTCACAA3' |
| pMI3 | 5'CCCTGAGTGTCAGATACAGCCCAGTAG3' |
| pMI2 | 5'GCAGGTGGTCAGCCAAGTCTGC3' |
| pDK | 5'TCTGCCAGTTTCCACCGCCTTTAGGT3' |
| pPL1 | 5'TACAGGCCACACCTAGTTTCCATCGTTTAC3' |
| pAL | 5'CTGCTGTTAAAGAGTCTGGCTCAACCAGAT3' |
| pAP | 5'CCCCTAGCTTTCGTCCCTCAGTGTCAGT3' |
| pNOS | 5'GCTCAACCARATMARAGCAGTGGAAACTA3' |
| pPL2 | 5'CAATCATTCCGGATAACGCTTGCATCC3' |
| pUN | 5'CCGTMTTACCGCGGCTGCTGGCA3' |

[1] the primers complememtary to these probe sequences were spoted on the membranes Hybridization and Chromogenic Detection.

Half a $\mu$l (100 pmol/$\mu$l) of primers complementary to the primers used in the labeling reaction were spotted onto membrane strips (4×5 cm) Hybon (Amersham), and then U. V. cross-linked with 5000 joule/$cm^2$. The strips were prehybridized for 2 hours at 37° C. in a prehybridization solution containing 0.7×SSC, 1×SPEP, 5×Denhardts and 100 $\mu$g/ml heterologous DNA. The products from the cyclic labeling reactions were added to 0.5 ml hybridization solution (0.7×SSC, 1×SPEP, 1×Denhardts, 10% Dextran sulfate and 100 $\mu$g/ml heterologous DNA) in a 2 ml microcentrifuge tube, and denatured at 95° C. for 5 min. The strips were added, and the incubation continued with gentle inversion for 2 hours at 37° C. The membrane strips were washed in 50 ml (1×SSC and 1% SDS), then in 50 ml (0.1×SSC and 0.1% SDS), and finally twice in 50 ml (0.10 M Tris-HCl [pH 7.5] and 0.15 M NaCl). Each washing was performed by brief vortexing at room temperature.

For antibody detection the membrane strips were blocked with 20 ml (0.10 M Tris-HCl [pH 7.5], 0.15 M NaCl and 0.5% skimmed milk) for 1 hour and incubated in 20 ml of the same buffer containing 1/1000 of Antifluorescein-HRP Conjugate (NEN) for an additional 1 hour. The membrane strips were washed 3 times by brief vortexing in 50 ml (0.10 M Tris-HCl [pH 7.5] and 0.15 M NaCl). The chromogenic reaction was done with the RENAISSANCE 4CN Plus For Chromogenic Detection of HRP for 5 min, according to the manufacturers recommendations (NEN).

The relative signal strengths were determined by scanning the membranes with an Agfa snapscanner 600, and analyzed using the Gel-Pro ANALYZER sofware (Media Cybernetics, Silver Spring, Md.).

Validation of the Probe Labeling Assay on Pure Cultures.

The probe labeling assay was applied on 8 different cyanobacterial strains representing the major lineages. The outgroup Chlorobium sp. was included as an additional control of the specificity of the probes. Approximately 5% of the DNA purified form the unialgal cultures were amplified with the universal primer-pair CC-CD in a 50 µl PCR reaction volume. The products were visualized on a 1.5% ethidium bromide-stained agarose gel, prior to the labeling, to confirm the amplification reaction. All of the samples were uniformly amplified, yielding a strong band at approx. 600 bp, with no visible additional bands.

Figure 5:
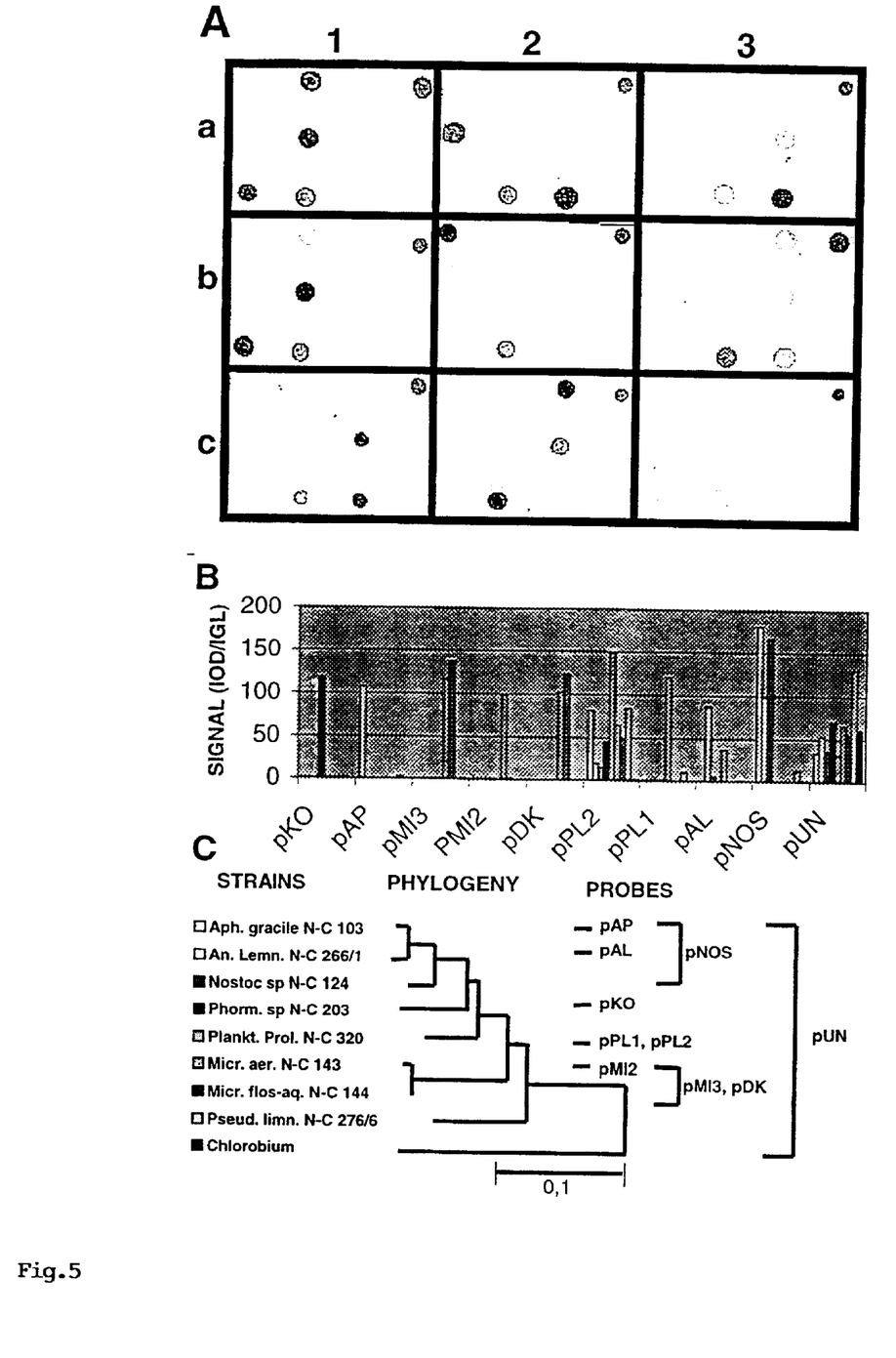

Related to the probe-labeling assay, the universal probe pUN was labeled relatively uniformly (with an exception for Pseudanabaena limnetica NIVA-CYA 276/6) for the strains tested (FIG. 5A). This probe was also labeled for the outgroup Chlorobium sp. Except for the probe pPL2, the different cyanobacteria specific probes gave signals as expected from their phylogenetic position (FIG. 5B and C). The low specificity of pPL2 may be due to the fact that the hybridization temperature used was not optimal for this probe. Generally, however, there was a high signal to noise ratio in the assay. For instance, there is only one base-pair difference between M. aeruginosa strains NIVA-CYA 143 and 144. Probe pMI2 distinguished NIVA-CYA 143 and 144 with a signal to noise ratio of 80.

The incorporation efficiency of fluorescently labeled dideoxy nucleotides is sequence dependent. There are also differences in the probe-labeling due to probe-target hybridrzation efficiencies. The base composition and the melting point, in addition to the sequences flanking the probe region, affect the probe hybridisation. The different labeling efficiencies ranged from 1.0 to 5, as determined relative to the labeling of the universal probe pUN for the probes developed in this work. For the respective probes, the efficiencies were as follows; pKO—1.7, pMl3—2.2, pMl2—1.4, pDK—1.9, pPL1—4.0, pAL—1.6, pAP—3.3, pNOS—4.3, and pPL2—4.9.

Distribution of Cyanobacteria From 7 Selected Localities.

The generality of the sample preparation and probe labeling strategies were tested on water samples from 7 different localities, ranging from water with a moderate level of plant biomass (mesotrophic) to water with a high biomass content (eutrophic).

Three samples were collected from each sampling site. The cell concentration and DNA purification were performed as described above for all three samples in parallel. Ribosomal DNA was amplified from 90,9, and 1% of the purified material. Amplification reactions were obtained for ØstensjØvatnet v Oslo, GjærsjØen and Årungen for 90% of the purified DNA. For 9% of the material all the samples were amplified, except the samples from Langen, while for 1% amplification reactions were obtained for all the samples.

Figure 6:
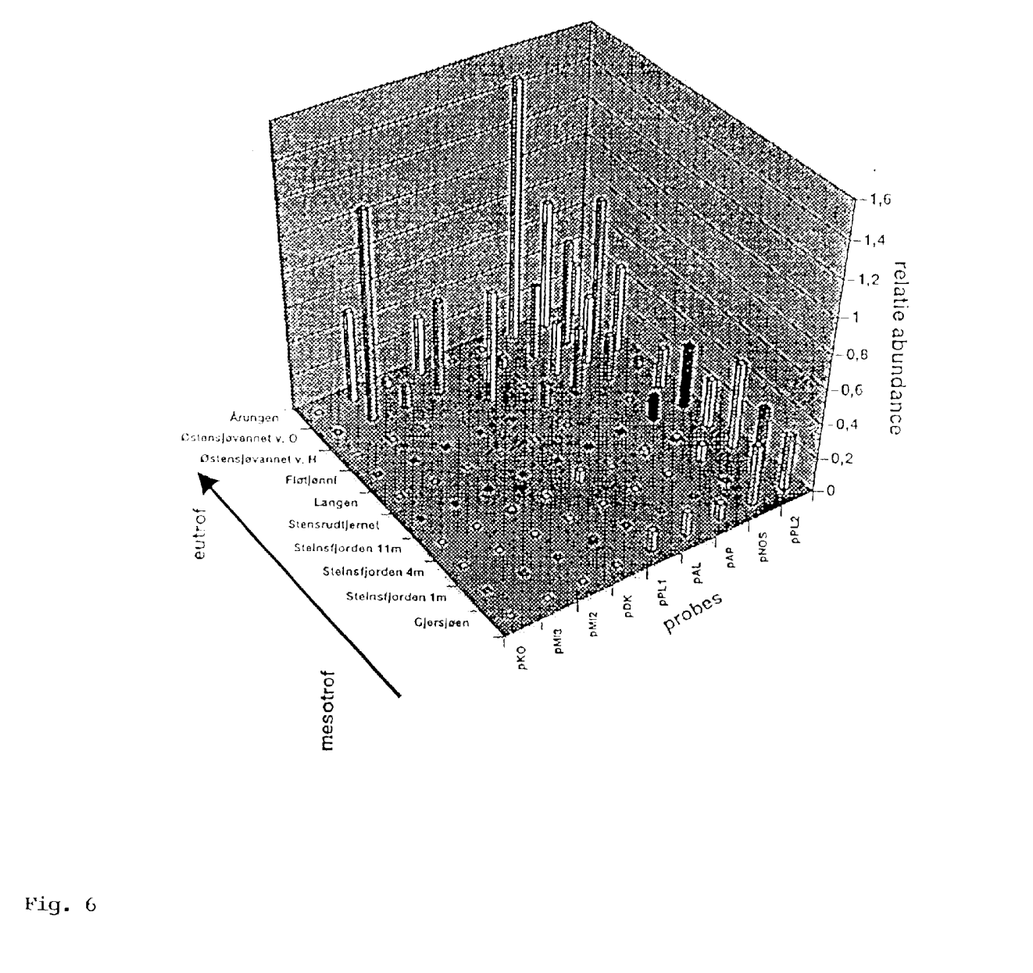
FIG. 6—shows a water profile analysis for 7 Norwegian lakes. The lakes range from those with a relatively low content of biomass (mesotroph) to lakes with high biomass content (eutroph). The signal intensities relative to the universal probe pUN were multiplied with a factor obtained from pure cultures to correct for differences in probe-labelling efficiencies to obtain the relative abundance of the different genotypes in the samples.

The average signal strength and standard deviation for the probe labelling were calculated for each investigated locality (based on the three collected samples). Since the different probes are not labelled with equal efficiently, this was adjusted for based on the relative labelling efficiencies obtained from the analyses of pure cultures (FIG. 6). The bars in this figure show the approximate relative composition of the determined genotypes in the sample. Because there is an unknown component of heterotrophic bacteria in some of the cultures used for correlation, the quantitation of the respective organisms may be an overestimate.

As a further verification of the probe-labelling assay the samples were also examined by microscopy. Here, the dominant species for each locality was determined based on morphological and cytological characteristics, according to the criteria given by Skulberg et al [Skulberg, O. M. Carmichael, W. W., Codd, G. A. and Skulberg R. (1993) Algal toxins in seafood and drinking water pp 145–164 Ed. Falconer I. R., London Academic Press Ltd]. There was generaly a good correlation between the groups of organisms in the sample, as determined by the genetic and the microscopic analyses. The 16S rDNA gene used in the genetic analysis, however, does not have enough sequence variation for discrimination to the species level. In addition, we could not distinguish between the morphologically defined genera Anabaena and Aphanizomenon with the probe-labelling assay. The reason for this is that the two positions used for discrimination do not follow the species designation. This can be due to that there have been several independent substitutions for the respective positions, that there have been recombination events in the 16S rDNA between the two probes, or that the species definition is not phyletically relevant. The hierarchical probe pNOS, on the other hand, seemed specific for the Nostoc group—including Anabaena and Aphanizomenon.

The Planktothrix specific probe pPL1 gave a relatively strong signal with the probe-labelling assay for lake Gjersoen, while this organism was not detected by the microscopic examinations of water from this lake. This dilference may be explained by the fact that samples for microscope analysis was concentrated through a 2 µm plankton net before the analysis, while for the genetic analysis the sample was analyzed directly. Furthermore, the cyanobaceria may not be distributed evenly in the lake, which may also explain the diuferences in the probe labeling and the microscopic examinations.

What is claimed is:

1. A method of detecting a target nucleotide sequence in a nucleic acid molecule which comprises:

(a) binding of an oligonucleotide probe to said nucleic acid molecule to provide a complex between the oligonucleotide probe and nucleic acid molecule;

(b) selective labeling of the bound oligonucleotide probe in the presence of said target nucleotide sequence;

(c) denaturation of the complex between the oligonucleotide probe and nucleic acid molecule;

(d) incubation of the labeled and any unlabeled oligonucleotide and a complementary sequence under conditions whereby labeled oligonucleotide hybridizes to the complementary sequence; and (e) subsequent detection of the label wherein detection of the label is indicative of detection of the target nucleotide sequence.

2. A method as claimed in claim 1 wherein, the complementary sequence of (d) is fully complementary to the oligonucleotide probe.

3. A method as claimed in claim 1 wherein the oligonucleotide probe is 20 to 30 nucleotides in length.

4. A method as claimed in claim 3 wherein the oligonucleotide probe is labelled by incorporation of a labelled nucleotide.

5. A method as claimed in claim 4 wherein the labelled nucleotide is a labelled dideoxynucleotide.

6. A method as claimed in claim 4 wherein selective labelling takes place in the presence of one or more labelled dideoxynucleotides and one or more unlabelled dideoxynucleotides.

7. A method as claimed in claim 6 wherein selective labelling takes place in the presence of one labelled didecxynculeotide and three unlabelled dideoxynucleotides.

8. A method as claimed in claim 7 wherein the oligonucleotide probe is designed with one or more mismatches at the 3'-end to non-target nucleotide sequences.

9. A method as claimed in claim 8 wherein a plurality of labelling steps are performed consecutively.

10. A method as claimed in claim 9 wherein the sequence complementary to the labelled oligonucleotide is immobilised on a solid support.

11. A method as claimed in claim 10 wherein the solid support is a membrane strip or nucleic acid chip.

12. A method as claimed in claim 11 wherein steps (a) to (e) are preceded by amplification of the nucleic acid molecule which contains the target sequence.

13. A method as claimed in claim 12 wherein the nucleic acid molecule which contains the target sequence is co-amplified with a competitor nucleic acid molecule.

14. A method as claimed in claim 13 wherein the competitor molecule comprises a recognition sequence which is complementary to a competitor oligonucleotide probe.

15. A method as claimed in claim 14 wherein the competitor oligonucleotide probe is selectively labelled after hybridization to the competitor molecule.

16. A method as claimed in claim 15 which additionally comprises hybridisation of the labelled competitor oligonucleotide to a complementary sequence and subsequent detection of the label.

17. A method as claimed in claim 16 wherein the sequences which are complementary to the oligonucleptide probes are immobilised on a solid support in discrete, pre-determined positions.

18. A method of determining the amount of a target nucleotide sequence in a nucleic acid molecule or the number of cells containing a target nucleotide sequence in a nucleic acid molecule which comprises (a) binding of an oligonucleotide probe to said nucleic acid molecule to provide a complex between the oligonucleotide probe and nucleic acid molecule;

(b) selective labeling of the bound oligonucleotide probe in the presence of said target nucleotide sequence;

(c) denaturation of the complex between the oligonucletoide probe and nucleic acid molecule;

(d) incubation of labeled and any unlabeled oligonucleotide and a complementary sequence under conditions whereby labeled oligonucleotide hybridizes to the complementary sequence;

(e) subsequent detection of the label; and (f) quantification of the label, wherein the quantity of the label is correlated with the amount of the target sequence or the number of cells containing the target sequence.

19. A method of detecting the presence of bacteria in a sample which comprises a method as claimed in claim 1, wherein the target sequence is a signature sequence within the genome of bacteria of interest and wherein detection of the target sequence is indicative of the presence of the bacteria of interest.

20. A method as claimed in claim 19 wherein the bacteria are cyanobacteria.

* * * * *